United States Patent
Huang et al.

(10) Patent No.: US 11,730,787 B2
(45) Date of Patent: Aug. 22, 2023

(54) METHOD FOR TREATING HIV/AIDS COMPLICATIONS SUCH AS VIRAL ENCEPHALOPATHY, DRUG-INDUCED ENCEPHALOPATHY, AND NEUROLOGICAL DISORDERS OF IMMUNOCOMPROMISED CONCURRENT OPPORTUNISTIC INFECTIONS INCLUDING MOTOR NERVE, SENSORY NERVE AND OPTIC NERVE DISORDERS

(71) Applicants: Ying-Chieh Huang, Taoyuan (TW); Chen-Yu Lee, Taipei (TW)

(72) Inventors: Ying-Chieh Huang, Taoyuan (TW); Chen-Yu Lee, Taipei (TW)

( * ) Notice: Subject to any disclaimer, the term of this patent is extended or adjusted under 35 U.S.C. 154(b) by 74 days.

(21) Appl. No.: 17/520,856

(22) Filed: Nov. 8, 2021

(65) Prior Publication Data
US 2023/0141424 A1    May 11, 2023

(51) Int. Cl.
| | |
|---|---|
| *A61K 36/8969* | (2006.01) |
| *A61K 36/258* | (2006.01) |
| *A61K 36/79* | (2006.01) |
| *A61K 36/725* | (2006.01) |
| *A61K 45/06* | (2006.01) |
| *A61K 36/70* | (2006.01) |
| *A61K 36/537* | (2006.01) |
| *A61K 36/484* | (2006.01) |
| *A61K 36/40* | (2006.01) |
| *A61P 31/18* | (2006.01) |
| *A61K 36/481* | (2006.01) |

(52) U.S. Cl.
CPC ........ *A61K 36/8969* (2013.01); *A61K 36/258* (2013.01); *A61K 36/40* (2013.01); *A61K 36/484* (2013.01); *A61K 36/537* (2013.01); *A61K 36/70* (2013.01); *A61K 36/725* (2013.01); *A61K 36/79* (2013.01); *A61K 45/06* (2013.01); *A61P 31/18* (2018.01); *A61K 36/481* (2013.01)

(58) Field of Classification Search
None
See application file for complete search history.

(56) References Cited

U.S. PATENT DOCUMENTS

2008/0063658 A1* 3/2008 Olalde Rangel ....... A61K 36/79
424/769

FOREIGN PATENT DOCUMENTS

| CN | 1143502 A | * | 2/1997 |
| CN | 1367003 A | * | 9/2002 |

OTHER PUBLICATIONS

Machine translation of CN-1367003-A.*
Machine translation of CN-1143502-A.*
Huang Ying-Chieh; Lin Yu-Jen; Lin Chi-Hong; Liu Wei-Hsiu; Ju Da-Tong; Liao Yan-Chih; Lee Chen-Yu, Case study on treatment of HIV / AIDS associated infectious meningitis, drug-induced aseptic meningitis, compromised immunity and neuro-cognitive disorder due to associated complications, Journal of Chinese Medical Acupuncture Science, 8(1), 72-83.Dec. 27, 2020.

* cited by examiner

*Primary Examiner* — H. Sarah Park
(74) *Attorney, Agent, or Firm* — Bacon & Thomas, PLLC

(57) ABSTRACT

The present invention relates to a method for treating HIV/AIDS complications including administering a first Chinese herbal medicine composition to a subject in need; wherein the first Chinese herbal medicine composition is an extract of a first mixture including *Polygonatum sibiricum*, *Astragalus membranaceus*, *Panax ginseng*, *Liriope spicata*, *Schisandra chinensis*, *Ziziphus zizyphus*, *Cornus officinalis*, *Fallopia multiflora*, and *Salvia miltiorrhiza*.

15 Claims, No Drawings

METHOD FOR TREATING HIV/AIDS COMPLICATIONS SUCH AS VIRAL ENCEPHALOPATHY, DRUG-INDUCED ENCEPHALOPATHY, AND NEUROLOGICAL DISORDERS OF IMMUNOCOMPROMISED CONCURRENT OPPORTUNISTIC INFECTIONS INCLUDING MOTOR NERVE, SENSORY NERVE AND OPTIC NERVE DISORDERS

BACKGROUND OF THE INVENTION

1. Field of the Invention

The present invention relates to method for treating HIV/AIDS complications.

2. Description of Related Art

Due to the potential of Chinese herbal medicine for treating disease, traditional Chinese herbal medicine has gradually attracted attention in recent years. The principle of applying Chinese herbal medicine is based on the practice of traditional Chinese medicine theory.

Human Immunodeficiency Virus (HIV) is a retrovirus and is divided into two types: HIV-1 and HIV-2. It invades cells having CD4 molecules, greatly reduces the body's immune function, and weakens the patient's immune system, thereby causing a variety of complications such as viral encephalopathy, drug-induced encephalopathy, and neurological disorders of immunocompromised concurrent opportunistic infections including motor nerve, sensory nerve and optic nerve disorders.

Currently, High Active Antiretroviral Therapy (HAART), also known as cocktail therapy, is provided for patients infected with HIV to effectively control the condition, reduce mortality, and prolong the lifetime of patients. However, the abovementioned therapies can only control the disease, but cannot completely cure the disease. The virus may still exist in lymph nodes, macrophages, central nervous system, or other tissues and cells, which cause viral encephalopathy, drug-induced encephalopathy, and immunocompromised concurrent opportunistic infections, or multiple system comorbidities, resulting in motor nerve, sensory nerve, or optic nerve dysfunction.

Therefore, there is an urgent need to provide a novel therapeutic drug for patients having HIV/AIDS complications, so as to alleviate or improve the aforementioned HIV/AIDS complications, improve the quality of life of the patients, or prolong the lifetime of the patients.

SUMMARY OF THE INVENTION

The present invention relates to a composition and method for treating HIV/AIDS complications, which can alleviate or improve the HIV/AIDS complications, improve the quality of life of the patients, or prolong the lifetime of the patients.

The present invention provides a first Chinese medicine composition for treating HIV/AIDS complications, and the first Chinese medicine composition comprises an extract of a first mixture comprising *Polygonatum sibiricum*, *Astragalus membranaceus*, *Panax ginseng*, *Liriope spicata*, *Schisandra chinensis*, *Ziziphus zizyphus*, *Cornus officinalis*, *Fallopia multiflora*, and *Salvia miltiorrhiza*.

The present invention further provides a method for treating HIV/AIDS complications, comprising: administering said first Chinese medicine composition to a subject in need thereof. Particularly, the method comprises administering an effective amount of said first Chinese medicine composition to a subject in need thereof.

The first Chinese medicine composition of the present invention may be prepared by the following steps: providing the first mixture; mixing the first mixture with water to form a second mixture; heating the second mixture to obtain a first crude extract; and filtering the first crude extract to keep a first liquid extract and obtain the first Chinese medicine composition.

The first mixture of the present invention may comprise 4-6 parts by weight of *Polygonatum sibiricum*, 2-4 parts by weight of *Astragalus membranaceus*, 2-4 parts by weight of *Panax ginseng*, 4-6 parts by weight of *Liriope spicata*, 1-3 parts by weight of *Schisandra chinensis*, 2-4 parts by weight of *Ziziphus zizyphus*, 2-4 parts by weight of *Cornus officinalis*, 2-4 parts by weight of *Fallopia multiflora*, and 2-4 parts by weight of *Salvia miltiorrhiza*.

The he first mixture of the present invention may further comprise *Glycyrrhizae radix*. In one aspect of the present invention, the first mixture may further comprise 2-4 parts by weight of *Glycyrrhizae radix*.

The present invention further provide a second Chinese medicine for treating HIV/AIDS complications, and the second Chinese medicine composition is an extract of a third mixture which may comprise *Astragalus membranaceus*, *Angelica sinensis*, *Ligusticum striatum*, *Paeonia veitchii*, *Salvia miltiorrhiza*, *Ginkgo biloba*, *Gastrodia elata*, *Uncariae ramulus cum uncis*, *Leonurus japonicas*, *Aralia cordata*, and *Achyranthes bidentata*.

The method for treating HIV/AIDS complications according to the present invention may further comprise administering said second Chinese medicine composition to a subject in need thereof. Particularly, the method comprises administering an effective amount of said second Chinese medicine composition to a subject in need thereof.

The second Chinese medicine composition of the present invention may be prepared by the following steps: providing the third mixture;

mixing the third mixture with water to form a fourth mixture; heating the fourth mixture to obtain a second crude extract; and filtering the second crude extract to keep a second liquid extract and obtain the second Chinese medicine composition.

The third mixture of the present invention may comprise 19-21 parts by weight of *Astragalus membranaceus*, 3-5 parts by weight of *Angelica sinensis*, 3-5 parts by weight of *Ligusticum striatum*, 3-5 parts by weight of *Paeonia veitchii*, 3-5 parts by weight of *Salvia miltiorrhiza*, 3-5 parts by weight of *Ginkgo biloba*, 2-4 parts by weight of *Gastrodia elata*, 2-4 parts by weight of *Uncariae ramulus cum uncis*, 2-4 parts by weight of *Leonurus japonicas*, 2-4 parts by weight of *Aralia cordata*, and 2-4 parts by weight of *Achyranthes bidentata*.

The present invention further provides a third Chinese medicine composition for treating HIV/AIDS complications, and the third Chinese medicine composition is an extract of a fifth mixture which may comprise *Lycii radicis cortex*, *Cortex moutan radices*, *Angelica sinensis*, *Ligusticum striatum*, *Paeonia veitchii*, *Rehmannia glutinosa*, *Scutellaria baicalensis*, *Atractylodes lancea*, *Glycyrrhiza uralensis*, *Gastrodia elata*, *Lycium chinense*, *Dendrobium nobile*, *Wolfiporia extensa*, *Cicadae Periostracum*, and *Senecio scandens*.

The method for treating HIV/AIDS complications according to the present invention may further comprise administering said third Chinese medicine composition to a subject in need thereof. Particularly, the method comprises administering an effective amount of said third Chinese medicine composition to a subject in need thereof.

The third Chinese medicine composition of the present invention may be prepared by the following steps: providing the fifth mixture; mixing the fifth mixture with water to form a sixth mixture; heating the sixth mixture to obtain a third crude extract; and filtering the third crude extract to keep a third liquid extract and obtain the third Chinese medicine composition.

The fifth mixture of the present invention may comprise 4-6 parts by weight of *Lycii radicis cortex*, 4-6 parts by weight of *Cortex moutan radices*, 2-4 parts by weight of *Angelica sinensis*, 2-4 parts by weight of *Ligusticum striatum*, 2-4 parts by weight of *Paeonia veitchii*, 2-4 parts by weight of *Rehmannia glutinosa*, 2-4 parts by weight of *Scutellaria baicalensis*, 3-5 parts by weight of *Atractylodes lancea*, 2-4 parts by weight of *Glycyrrhiza uralensis*, 2-4 parts by weight of *Gastrodia elata*, 2-4 parts by weight of *Lycium chinense*, 3-5 parts by weight of *Dendrobium nobile*, 2-4 parts by weight of *Wolfiporia extensa*, 1-3 parts by weight of *Cicadae Periostracum*, and 2-4 parts by weight of *Senecio scandens*.

The method for treating HIV/AIDS complications may further comprises administering a medicine pillow or a medicine mask to the subject in need thereof, the medicine-filled pillow may comprise a seventh mixture comprising *Pinus tabuliformis, Fallopia multiflora, Cortex albiziae*, and *Nardostachys chinensis batal*; and, the medicine mask may comprise a eighth mixture comprising *Agastache rugosa, Ephedra sinica, Magnolia liliflora desr, Saposhnikovia divaricate, Mentha canadensis, Xanthium strumarium, Scutellaria baicalensis, Angelica dahurica, Ligusticum striatum, Boswellia carter, Chrysanthemum morifolium, Senna obtusifolia*, and *Cymbopogon*.

The medicine pillow of the present invention may be prepared by the following steps: providing and grinding the seventh mixture to form a powder mixture; mixing the powder mixture and a thermal conductive substance to form a ninth mixture; and filling the ninth mixture into a bag to obtain a medicine pillow. The present invention does not impose particular limitation on the material of the thermal conductive substance, provided that the thermal conductive substance has the function of heat preservation. In one embodiment of the present invention, the thermal conductive substance may be red beans (adzuki beans). The medicine pillow provided in the present invention may be heated before use.

The seventh mixture of the present invention may comprise 20-40 parts by weight of *Pinus tabuliformis*, 20-40 parts by weight of *Fallopia multiflora*, 20-40 parts by weight of *Cortex albiziae*, and 20-40 parts by weight of *Nardostachys chinensis batal*.

The medicine mask of the present invention may be prepared by the following steps: providing the eighth mixture; and filling the eighth mixture into a medicine bag to obtain a medicine mask. Herein, the medicine mask provided by the present invention may be heated before use.

The eighth mixture of the present invention may comprise 1-2 parts by weight of *Agastache rugosa*, 1-2 parts by weight of *Ephedra sinica*, 0.5-1.5 parts by weight of *Magnolia liliflora desr*, 0.5-1.5 parts by weight of *Saposhnikovia divaricate*, 0.5-1.5 parts by weight of *Mentha Canadensis*, 0.5-1.5 parts by weight of *Xanthium strumarium*, 0.5-1.5 parts by weight of *Scutellaria baicalensis*, 2-4 parts by weight of *Angelica dahurica*, 1.5-2.5 parts by weight of *Ligusticum striatum*, 0.5-1.5 parts by weight of *Boswellia carter*, 0.5-1.5 parts by weight of *Chrysanthemum morifolium*, 0.5-1.5 parts by weight of *Senna obtusifolia*, and 0.5-1.5 parts by weight of *Cymbopogon*.

In the present invention, the part by weight of the first mixture, the third mixture and the fifth mixture may be 2.5-5 grain per part, preferably 3-4 gram per part, more preferably 3.75 gram per part, but the present invention is not limited thereto.

In the present invention, the part by weight of the seventh mixture and the eighth mixture may be 0.5-3 gram per part, preferably 0.5-2 gram per part, more preferably 1 gram per part, but the present invention is not limited thereto.

In the present invention, the term "treat" or "treatment" used herein refers to administer the first Chinese medicine composition, the second Chinese medicine composition, and the third Chinese medicine composition of the present invention to a subject in need thereof, or administer the medicine pillow or medicine mask to a subject in need thereof, thereby inhibiting, curing, improving, healing, ameliorating, alleviating, changing, or affecting HIV/AIDS complications. For instance, the method of the present invention may be used to inhibit HIV/AIDS complications.

Herein, the HIV/AIDS complications may include pneumonia, meningitis, retinitis, hearing defect, viral encephalopathy, drug-induced encephalopathy, neurological disorders of immunocompromised concurrent opportunistic infections (including motor nerve, sensory nerve and optic nerve disorders), or immunocompromised disease, but the present invention is not limited thereto.

In one aspect of the present invention, the HIV/AIDS complications may be viral encephalopathy, drug-induced encephalopathy, or neurological disorders of immunocompromised concurrent opportunistic infections (including motor nerve, sensory nerve and optic nerve disorders).

In the present invention, the term "effective amount" used herein refers to a necessary dose leading to expected therapeutic effects in a subject treated, and it may be changed depending on the route of administration, the use of excipients and the combined use with other medicaments.

The first Chinese medicine composition, the second Chinese medicine, and the third Chinese medicine composition of the present invention may be administered via oral administration or injection. However, the present invention is not limited thereto.

The first Chinese medicine composition, the second Chinese medicine, and the third Chinese medicine composition of the present invention may further comprise pharmaceutically acceptable carrier, stabilizer, thinner, dispersant, suspending agent, thickener, excipient or the combination thereof. However, the present invention is not limited thereto.

In the present invention, the term "acceptable" used herein means that it should be compatible with the first Chinese medicine composition, the second Chinese medicine, and the third Chinese medicine composition, preferably be able to stabilize the first Chinese medicine composition, the second Chinese medicine, and the third Chinese medicine composition, and cannot jeopardize the subject treated.

The present invention is not restrictive of the method for decocting Chinese medicine, and it can be implemented in any known manner. The present invention is not restrictive of the method for heating the Chinese medicine, and it can be implemented by any known method, such as direct heating and double-boiling.

DETAILED DESCRIPTION OF THE PREFERRED EMBODIMENT

The following embodiments are meant to explain the implementation of the present invention, they should be construed as descriptive merely, and should not restrict the remaining part of the present invention. The person having ordinary skills in the art can easily understand other advantages and effects of the present invention. The present invention may also be implemented or applied by other different embodiments, and various details in this specification may also be modified and changed according to different viewpoints and applications without departing from the spirit of the invention.

Unless specified otherwise, all technical and scientific terms described in the specification and claims of the present invention are defined as follows. In the present invention, the singular term and "the", may refer to one or more objects, unless specified otherwise. In addition, the term "comprise" is an open-ended transition word which does not limit to the items listed. The foregoing paragraphs are only systematic references and should not be construed as limitations for the subject of the invention. Unless specified otherwise, the materials used in the present invention are commercially available and easy to obtain. Possible sources for obtaining the materials are listed below and it is exemplary only.

Preparation Example 1

Five parts by weight of *Polygonatum sibiricum*, 3 parts by weight of *Astragalus membranaceus*, 3 parts by weight of *Panax ginseng*, 5 parts by weight of *Liriope spicata*, 1.5 parts by weight of *Schisandra chinensis*, 3 parts by weight of *Ziziphus zizyphus*, 3 parts by weight of *Cornus officinalis*, 3 parts by weight of *Fallopia multiflora*, and 3 parts by weight of *Salvia miltiorrhiza* were provided to form a Mixture-1; the Mixture-1 was mixed with 42 parts by weight of water and decocted for 2.5 hours to form a Crude extract-1 being about 40 parts by weight; the Crude extract-1 was filtered and the filtrate was collected to obtain the Chinese medicine composition-1 of the present preparation example. In the present preparation example, the part by weight was 3.75 grain per part.

Preparation Example 2

The Mixture-1 of Preparation Example 1 was added with 3 parts by weight of *Glycyrrhizae radix* to obtain a Mixture-2 of the present preparation example; followed by extraction in a similar manner to Preparation Example 1 in order to obtain a Chinese medicine composition-2 of the present preparation example. In the present preparation example, the part by weight was 3.75 gram per part.

Preparation Example 3

Twenty parts by weight of *Astragalus membranaceus*, 4 parts by weight of *Angelica sinensis*, 4 parts by weight of *Ligusticum striatum*, 4 parts by weight of *Paeonia veitchii*, 4 parts by weight of *Salvia miltiorrhiza*, 4 parts by weight of *Ginkgo biloba*, 3 parts by weight of *Gastrodia elata*, 3 parts by weight of *Uncariae ramulus cum uncis*, 3 parts by weight of *Leonurus japonicas*, 3 parts by weight of *Aralia cordata*, and 3 parts by weight of *Achyranthes bidentata* were provided to form a Mixture-3; and, the Mixture-3 was mixed with 53 parts by weight of water and decocted for 2.5 hours to form a Crude extract-3 being about 40 parts by weight; the Crude extract-3 was filtered and the filtrate was collected to obtain the Chinese medicine composition-3 of the present preparation example. That *Leonurus japonicus*, *Ligusticum striatum*, *Aralia cordata*, and *Salvia miltiorrhiza* were added to invigorate blood and diuresis; *Achyranthes bidentata* was added to improve blood circulation in the lower human body; *Ginkgo biloba* was added to invigorate blood and improve microcirculation; *Gastrodia elata* and *Uncariae ramulus cum uncis* were added as ingredients for the treatment of brain diseases. In addition, the part by weight is 3.75 grain per part in the present preparation example.

Preparation Example 4

Five parts by weight of *Lycii radicis cortex*, 5 parts by weight of *Cortex moutan radices*, 3 parts by weight of *Angelica sinensis*, 3 parts by weight of *Ligusticum striatum*, 3 parts by weight of *Paeonia veitchii*, 3 parts by weight of *Rehmannia glutinosa*, 3 parts by weight of *Scutellaria baicalensis*, 4 parts by weight of *Atractylodes lancea*, 3 parts by weight of *Glycyrrhiza uralensis*, 3 parts by weight of *Gastrodia elata*, 3 parts by weight of *Lycium chinense*, 4 parts by weight of *Dendrobium nobile*, 3 parts by weight of *Wolfiporia extensa*, 1.5 parts by weight of *Cicadae Periostracum*, and 3 parts by weight of *Senecio scandens* were provided to form a Mixture-4; and, the Mixture-4 was mixed with 43 parts by weight of water and decocted for 2.5 hours to form a Crude extract-4 being about 40 parts by weight; the Crude extract-4 was filtered and the filtrate was collected to obtain the Chinese medicine composition-4 of the present preparation example. In the present preparation example, the part by weight was 3.75 grain per part.

Preparation Example 5

Thirty parts by weight of *Pinus tabuliformis*, 30 parts by weight of *Fallopia multiflora*, 30 parts by weight of *Cortex albiziae*, and 30 parts by weight of *Nardostachys chinensis batal* were provided to form a Mixture-5; the Mixture-5 was ground to obtain a powder mixture; the powder mixture was mixed with 3000 parts by weight of red beans and then the mixture was filled into a pillow case to obtain a medicine pillow. The way to use this medicine pillow was: microwave heating the medicine pillow for about 3-4 minutes; and applying the medicine pillow to the occipital bone and cervical spine of the subject for hot compress for 30-40 minutes, thereby promoting the vertebral artery and improving the blood supply to the back half of the brain. In addition, the part by weight was 1 gram per part in the present example.

Preparation Example 6

Fifteen parts by weight of *Agastache rugosa*, 15 parts by weight of *Ephedra sinica*, 10 parts by weight of *Magnolia liliflora desr*, 10 parts by weight of *Saposhnikovia divaricate*, 10 parts by weight of Mentha Canadensis, 10 parts by weight of Xanthium strumarium, 10 parts by weight of *Scutellaria baicalensis*, 30 parts by weight of *Angelica dahurica*, 20 parts by weight of *Ligusticum striatum*, 10 parts by weight of *Boswellia carter*, 10 parts by weight of *Chrysanthemum morifolium*, 10 parts by weight of *Senna obtusifolia*, and 10 parts by weight of *Cymbopogon* were provided to form a Mixture-6; and, 20 parts by weight of the Mixture-6 was taken and filled into a medicine bag to obtain a medicine mask. The way to use said medicine mask was: microwave heating the medicine mask before use; and, placing the medicine mask on the chest, nose or eyes to promote blood circulation in the carotid or ophthalmic artery, thereby promoting blood supply to the head, face and eyes. In addition, the part by weight was 1 grain per part in the present example.

Embodiment 1

The patient of Embodiment 1 was a patient infected with HIV. The patient had dry mouth, body dryness-heat, itchy skin and multiple rashes due to opportunistic infection.

A treatment of the present invention applied to the patient of Embodiment 1 was described below. From day one, a total amount of the Chinese medicine composition-1 of Preparation Example 1 was administered to the patient every day, wherein the total amount was divided into aliquots for bis in die administration. A follow-up report indicated that the patient still took the medicine as of the reporting date; the symptoms of dry mouth and body dryness-heat in the patient were alleviated; and, the skin no longer had itching and rash.

Embodiment 2

The patient of Embodiment 1 was a patient infected with HIV, and the patient suffered from chest tightness, palpitation, and pale complexion due to opportunistic infections.

A treatment of the present invention applied to the patient of Embodiment 2 was described below. From day one, a total amount of the Chinese medicine composition-2 of Preparation Example 2 was administered to the patient every day, wherein the total amount was divided into aliquots for bis in die administration. A follow-up report indicated that the patient still took the medicine as of the reporting date; the patient's symptoms of chest tightness and palpitation were significantly relieved, the heart rate was back to normal and the complexion was ruddy.

Embodiment 3

The patient of Embodiment 3 was a patient infected with HIV, and the patient suffered from multiple pneumonia, respiratory failure, and sepsis due to opportunistic infections.

A treatment of the present invention applied to the patient of Embodiment 3 was described below. From day one, the total amount of the Chinese medicine composition-1 of Preparation Example 1 and Chinese medicine composition-3 of Preparation Example 3 were administered to the patient every day, wherein the total amount was divided into aliquots for bis in die administration. A follow-up report indicated that the patient still took the medicine as of the reporting date; the patient's infection of sepsis was significantly relieved; and, the patient was able to breathe easily without difficulty. In addition, the patient's life had returned to normal.

Embodiment 4

The patient of Embodiment 4 was a patient infected with HIV, and the patient was unable to stand for long periods due to the weakness of lower limbs caused by opportunistic infections.

The treatment of the present invention applied to the patient of Embodiment 4 was described below. From day one, the total amount of the Chinese medicine composition-1 of Preparation Example 1 and Chinese medicine composition-3 of Preparation Example 3 were administered to the patient every day, wherein the total amount was divided into aliquots for bis in die administration; and, the medicine pillow of Preparation Example 5 was applied to the patient two times a day to promote vertebral artery circulation, thereby improving the blood supply to the back half of the brain. A follow-up report indicated that the patient still took the medicine as of the reporting date; the weakness of lower limbs was significantly relieved; and, the patient was able to walk normally and even walk briskly.

Embodiment 5

The patient of Embodiment 5 was a patient infected with HIV, and the patient's hands and feet were weak and numb; and, the patient's joints of the fingers were deformed and unable to grasp objects.

The treatment of the present invention applied to the patient of Embodiment 5 was described below. From day one, the total amount of the Chinese medicine composition-1 of Preparation Example 1, Chinese medicine composition-3 of Preparation Example 3, and Chinese medicine composition-4 of Preparation Example 4 were administered to the patient every day, wherein the total amount was divided into aliquots for bis in die administration; and, the medicine pillow of Preparation Example 5 was applied to the patient two times a day. A follow-up report indicated that the patient still took the medicine as of the reporting date; the numbness of the patient's hands and feet disappeared, the patient was able to stand, and the joint deformity was significantly improved.

Embodiment 6

The patient of Embodiment 6 was a patient infected with HIV, and a blurred vision was in the patient's left eye due to optic nerve damage.

The treatment of the present invention applied to the patient of Embodiment 6 was described below. From day one, the total amount of the Chinese medicine composition-3 of Preparation Example 3 and Chinese medicine composition-4 of Preparation Example 4 were administered to the patient every day, wherein the total amount was divided into aliquots for bis in die administration; and, the medicine mask of Preparation Example 6 was applied to the patient two times a day. A follow-up report indicated that the patient still took the medicine as of the reporting date; and, the patient's symptom of blurred vision has been completely relieved.

Embodiment 7

The patient of Embodiment 7 was a patient infected with HIV, the patient suffered from hearing loss and binocular retinitis due to meningitis, and almost lost sight in both eyes.

The treatment of the present invention applied to the patient of Embodiment 7 was described below. From day one, the total amount of the Chinese medicine composition-1 of Preparation Example 1, Chinese medicine composition-3 of Preparation Example 3 and Chinese medicine composition-4 of Preparation Example 4 were administered to the patient every day, wherein the total amount was divided into aliquots for bis in die administration; and, the medicine mask of Preparation Example 6 was applied to the patient two times a day. A follow-up report indicated that the patient still took the medicine as of the reporting date; the patient's hearing loss was significantly relieved; and, the patient's eyes were able to see the shape of an object.

Embodiment 8

The patient of Embodiment 8 was a patient infected with HIV. The patient was unable to walk due to neurological disability, relied on a wheelchair to move and had incontinence of urine and feces. The patient's optic nerves were damaged, and the patient almost blind.

The treatment of the present invention applied to the patient of Embodiment 8 was described below. From day one, the total amount of the Chinese medicine composition-1 of Preparation Example 1, Chinese medicine composition-3 of Preparation Example 3 and Chinese medicine composition-4 of Preparation Example 4 were administered to the patient every day, wherein the total amount was divided into aliquots for bis in die administration, the medicine pillow of Preparation Example 5 was applied to the patient two times a day; and, the medicine mask of Preparation Example 6 was applied to the patient two times a day. A follow-up report indicated that the patient still took the medicine as of the reporting date; the patient's Modified Rankin Scale (mRS) score was recovered from 5 to 0 after the treatment. In addition, said patient's Barthel Index (Barthel Index) score was improved from 0 to 100 after the treatment. At present, the patient was able to walk normally and do the activities of daily living alone, and the patient's vision was restored.

Although the present invention has been explained in relation to its preferred embodiment, it is to be understood that many other possible modifications and variations can be made without departing from the spirit and scope of the invention as hereinafter claimed.

What is claimed is:

1. A method for treating symptoms of HIV/AIDS complications, comprising:
   administering an effective amount of a first Chinese medicine composition to a subject in need thereof;
   wherein, the first Chinese medicine composition is an extract of a first mixture comprising 4-6 parts by weight of *Polygonatum sibiricum,* 2-4 parts by weight of *Astragalus membranaceus,* 2-4 parts by weight of *Panax ginseng,* 4-6 parts by weight of *Liriope spicata,* 1-3 parts by weight of *Schisandra chinensis,* 2-4 parts by weight of *Ziziphus zizyphus,* 2-4 parts by weight of *Cornus officinalis,* 2-4 parts by weight of *Fallopia multiflora,* and 2-4 parts by weight of *Salvia miltiorrhiza.*

2. The method of claim 1, wherein the first Chinese medicine composition is prepared by the following steps:
   providing the first mixture;
   mixing the first mixture with water to form a second mixture;
   heating the second mixture to obtain a first crude extract; and
   filtering the first crude extract to keep a first liquid extract and obtain the first Chinese medicine composition.

3. The method of claim 1, wherein the first mixture further comprises *Glycyrrhizae radix.*

4. The method of claim 3, wherein the first mixture further comprises 2-4 parts by weight of *Glycyrrhizae radix.*

5. The method of claim 1, further comprising administering an effective amount of a second Chinese medicine composition to the subject in need thereof; wherein, the second Chinese medicine composition is an extract of a third mixture comprising 19-21 parts by weight of *Astragalus membranaceus,* 3-5 parts by weight of *Angelica sinensis,* 3-5 parts by weight of *Ligusticum striatum,* 3-5 parts by weight of *Paeonia veitchii,* 3-5 parts by weight of *Salvia miltiorrhiza,* 3-5 parts by weight of Ginkgo biloba, 2-4 parts by weight of *Gastrodia elata,* 2-4 parts by weight of *Uncariae ramulus cum uncis,* 2-4 parts by weight of *Leonurus japonicas,* 2-4 parts by weight of *Aralia cordata,* and 2-4 parts by weight of *Achyranthes bidentata.*

6. The method of claim 5, wherein the second Chinese medicine composition is prepared by the following steps:
   providing the third mixture;
   mixing the third mixture with water to form a fourth mixture;
   heating the fourth mixture to obtain a second crude extract; and
   filtering the second crude extract to keep a second liquid extract and obtain the second Chinese medicine composition.

7. The method of claim 5, further comprising administering an effective amount of a third Chinese medicine composition to the subject in need thereof; wherein, the third Chinese medicine composition is an extract of a fifth mixture comprising 4-6 parts by weight of *Lycii radicis cortex,* 4-6 parts by weight of *Cortex moutan radices,* 2-4 parts by weight of 2-4 parts by weight of *Angelica sinensis,* 2-4 parts by weight of *Ligusticum striatum,* 2-4 parts by weight of *Paeonia veitchii,* 2-4 parts by weight of *Rehmannia glutinosa,* 2-4 parts by weight of *Scutellaria baicalensis,* 3-5 parts by weight of *Atractylodes lancea,* 2-4 parts by weight of *Glycyrrhiza uralensis,* 2-4 parts by weight of *Gastrodia elata,* 2-4 parts by weight of *Lycium chinense,* 3-5 parts by weight of *Dendrobium nobile,* 2-4 parts by weight of *Wolfiporia extensa,* 1-3 parts by weight of *Cicadae Periostracum,* and 2-4 parts by weight of *Senecio scandens.*

8. The method of claim 7, wherein the third Chinese medicine composition is prepared by the following steps:
   providing the fifth mixture;
   mixing the fifth mixture with water to form a sixth mixture;
   heating the sixth mixture to obtain a third crude extract; and
   filtering the third crude extract to keep a third liquid extract and obtain the third Chinese medicine composition.

9. The method of claim 1, further comprising administering a medicine pillow or a medicine mask to the subject in need thereof, wherein the medicine-filled pillow comprises an effective amount of a seventh mixture comprising 20-40 parts by weight of *Pinus tabuliformis,* 20-40 parts by weight of *Fallopia multiflora,* 20-40 parts by weight of *Cortex albiziae,* and 20-40 parts by weight of *Nardostachys chinensis batal;* and, the medicine mask comprises an effective amount of an eighth mixture comprising 1-2 parts by weight of *Agastache rugosa,* 1-2 parts by weight of *Ephedra sinica,* 0.5-1.5 parts by weight of *Magnolia liliflora desr,* 0.5-1.5 parts by weight of *Saposhnikovia divaricate,* 0.5-1.5 parts by weight of *Mentha Canadensis,* 0.5-1.5 parts by weight of *Xanthium strumarium,* 0.5-1.5 parts by weight of *Scutellaria baicalensis,* 2-4 parts by weight of *Angelica dahurica,* 1.5-2.5 parts by weight of *Ligusticum striatum,* 0.5-1.5 parts by weight of *Boswellia carter,* 0.5-1.5 parts by weight of *Chrysanthemum morifolium,* 0.5-1.5 parts by weight of *Senna obtusifolia,* and 0.5-1.5 parts by weight of *Cymbopogon.*

10. The method of claim 9, wherein the medicine pillow is prepared by the following steps:

providing and grinding the seventh mixture to form a powder mixture; mixing the powder mixture and a thermal conductive substance to form a ninth mixture; and filling the ninth mixture into a bag to obtain a medicine pillow.

11. The method of claim 9, wherein the medicine mask is prepared by the following steps:

providing the eighth mixture; and filling the eighth mixture into a medicine bag to obtain a medicine mask.

12. The method of claim 1, wherein the HIV/AIDS complications comprise pneumonia, meningitis, retinitis, hearing defect, viral encephalopathy, drug-induced encephalopathy, neurological disorders of immunocompromised concurrent opportunistic infections, or immunocompromised disease.

13. The method of claim 1, wherein the Chinese medicine composition is administered via oral administration or injection.

14. The method of claim 5, wherein the second Chinese medicine composition is administered via oral administration or injection.

15. The method of claim 7, wherein the third Chinese medicine composition is administered via oral administration or injection.

* * * * *